| United States Patent [19] | [11] Patent Number: 4,925,971 |
|---|---|
| Aoki et al. | [45] Date of Patent: May 15, 1990 |

[54] METHOD FOR PRODUCING ALIPHATIC O-ARYLURETHANES

[75] Inventors: Toshiya Aoki; Hiroshi Ishida; Shinsuke Fukuoka, all of Kurashiki, Japan

[73] Assignee: Asahi Kasei Kogyo Kabushiki Kaisha, Osaka, Japan

[21] Appl. No.: 279,177

[22] Filed: Dec. 2, 1988

[30] Foreign Application Priority Data

Dec. 8, 1987 [JP] Japan ................................ 62-308744

[51] Int. Cl.$^5$ .......................................... C07C 125/075
[52] U.S. Cl. .................................... 560/137; 546/153; 546/292; 546/335; 549/285; 560/25; 560/28; 560/32; 560/115; 560/132; 560/133; 560/134; 560/135; 560/136
[58] Field of Search ............... 560/132, 133, 134, 135, 560/136, 137, 157, 158, 25, 28, 32, 115; 546/292, 335, 153; 549/285

[56] References Cited

U.S. PATENT DOCUMENTS

| | | | |
|---|---|---|---|
| 2,409,712 | 10/1946 | Schweitzer | 260/453 |
| 2,677,698 | 5/1954 | Deutschman | 260/432 |
| 2,806,051 | 9/1957 | Brockway | 260/471 |
| 3,873,553 | 3/1975 | Hearsey | 260/295 |
| 4,336,402 | 6/1982 | Falcone | 560/157 |

FOREIGN PATENT DOCUMENTS 2917493 11/1980 Fed. Rep. of Germany .
2943481 5/1981 Fed. Rep. of Germany .

*Primary Examiner*—Michael L. Shippen
*Attorney, Agent, or Firm*—Armstrong, Nikaido, Marmelstein, Kubovcik & Murray

[57] ABSTRACT

A method for producing aliphatic O-arylurethanes by the reaction of an aliphatic primary amine with an aromatic hydroxyl compound and urea. Ammonia produced as a by-product in the reaction is removed during the reaction so that the ammonia concentration of the reaction solution is maintained at 2 wt % or less.

14 Claims, 1 Drawing Sheet

METHOD FOR PRODUCING ALIPHATIC O-ARYLURETHANES

BACKGROUND OF THE INVENTION

1. Field of the Invention

This invention relates to a method for producing aliphatic O-arylurethanes widely used as masked isocyanates, or as precursors of aliphatic isocyanates. Particularly, this invention relates to a method for producing aliphatic O-arylurethanes characterized in that an aliphatic primary amine is reacted with an aromatic hydroxyl compound and urea while the ammonia produced as a by-product is removed from the reaction system so that the ammonia concentration of the reaction solution is maintained at 2 wt.% or less.

2. Discussion on Related Art

Hitherto, aliphatic O-arylurethanes have been produced by reacting an aromatic hydroxyl compound with an aliphatic isocyanate (for example, K. Iwata, Lecture on Plastic Materials 2, Polyurethane Resins, pp. 174~178, published by Nikkan Kogyo Shinbun-sha (Daily Industries News Co., Ltd.), 1969; K. C. Frisch, "Fundamental Chemistry and Catalysis of Polyurethanes", Polyurethane Technology, P. F. Bruins, Ed., Interscience Publishers, New York, 1969, pp. 11~12). The aliphatic isocyanate is obtained by reaction of the corresponding aliphatic primary amine with phosgene (see for example, Brit. Patent No. 1,077,031), so that this method has the following drawbacks: (1) phosgene, a deadly poison is used; (2) corrosive hydrogen chloride gas is produced as a by-product in large amounts; and (3) the product usually contains hydrolyzable chlorine compounds, and these by-products are extremely difficult to remove. Consequently, the method of obtaining aliphatic O-arylurethanes by the reaction of an aromatic hydroxyl compound with an aliphatic isocyanate has not been satisfactory.

U.S. Pat. No. 4,297,501 discloses a method for producing aliphatic O-arylurethanes without using phosgene by oxidative urethanation of a primary amine with carbon monoxide and an aliphatic alcohol or aromatic hydroxyl compound in the presence of a noble metal catalyst. This patent, however, discloses no examples in which the aromatic hydroxyl compound is used. This method also has several drawbacks: (1) poisonous carbon monoxide is used; and (2) since an expensive noble metal catalyst is used, it must be recovered from the resulting urethane products, and this recovery requires troublesome operations and is expensive.

U.S. Pat. No. 3,873,553 discloses a method for producing N-alkyl-O-arylurethanes by reacting N-alkyl-N',N'-dialkylurea with an aromatic hydroxyl compound and hydrogen chloride gas. This method also has drawbacks that highly corrosive hydrogen chloride gas and an expensive and special urea compound are used, and that recovery of the urethanes from N,N-dialkylamine hydrochloride, a by-product, requires troublesome operations and is expensive.

U.S. Pat. No. 2,677,698 discloses a method for producing aliphatic monourethanes without using phosgene in which N,N'-dialkylurea is produced in a first step by reacting an aliphatic primary monoamine with urea, and in a second step, the aliphatic monourethanes are produced by reacting N,N'-dialkylurea with a hydroxyl compound, and the primary amine, a by-product, is separated, recovered and recycled to the first step. This patent, however, discloses no examples in which the aromatic hydroxyl compound is used. This method is also not satisfactory to carry out industrially because the yield of the urethane is low, and the process is very troublesome, since the reaction is carried out in two steps and equipment for recycling the primary amine is required.

Some methods for producing aliphatic urethanes by reacting an aliphatic primary amine with a hydroxyl compound and urea in one step have been proposed. The aliphatic urethanes obtained by these methods, however, are not aliphatic O-arylurethanes, but aliphatic O-alkylurethanes. For example, U.S. Pat. No. 2,409,712 discloses a method for producing aliphatic O-alkylmonourethanes by reacting an aliphatic primary amine with urea with an aliphatic alcohol. German Patent Nos. 2,917,493 and 2,943,551 also discloses a method for producing aliphatic O-alkylpolyurethanes by reacting an aliphatic primary polyamine with an aliphatic, alicyclic or aralkyl alcohol in the presence of urea or a urea compound.

However, the aliphatic O-alkylurethanes produced by these methods, because they are thermally very stable, are difficult to decompose to the corresponding aliphatic isocyanates and alcohols. They are not, therefore, satisfactory to use as masked isocyanates or as precursors of aliphatic isocyanates.

In this respect, it is known that the aliphatic O-arylurethanes easily decompose to the corresponding aliphatic isocyanates and aromatic hydroxyl compounds (for example, O. Bayer, "Das DiisocyanatPolyadditions Verfahren", p. 12, 1963). However, a method for producing aliphatic O-arylurethanes by reacting an aliphatic primary amine with an aromatic hydroxyl compound and urea in one step was not known.

SUMMARY OF THE INVENTION

The present inventors have studied extensively a method for producing aliphatic O-arylurethanes by reacting an aliphatic primary amine with an aromatic hydroxyl compound and urea, and as a result, have discovered the following. The reaction, as exemplified by equation (I) below, in the case of the reaction of an aliphatic primary amine with urea and an aromatic monohydroxyl compound, is reversible and its equilibrium lies so far to the left (side of the starting materials), that removal of the ammonia by-produced is essential for the reaction to proceed; and the aromatic hydroxyl compound, which is a kind of acidic material binds with ammonia so strongly that removal of the ammonia is very difficult by the usual methods. The reaction is illustrated as follows:

$$R-(NH_2)_n + nNH_2CONH_2 + nArOH \underset{150°-280° C.}{\overset{-2nNH_3}{\rightleftarrows}} R-(NHCOOAr)_n \quad (I)$$

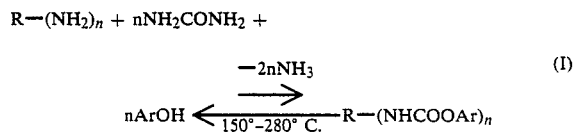

wherein n represents an integer of 1 or more, R represents an n valent aliphatic residue, and Ar represents mono-valent aromatic residue.

Further, the present inventors found that in the reaction of an aliphatic primary amine with urea and an aromatic hydroxyl compound, the aliphatic O-arylurethanes can be obtained in high yields by removing the ammonia by produced from the reaction system so that the ammonia concentration of the reaction solution is kept 2 wt% or less.

DETAILED DESCRIPTION OF PREFERRED EMBODIMENTS

Figure 1:
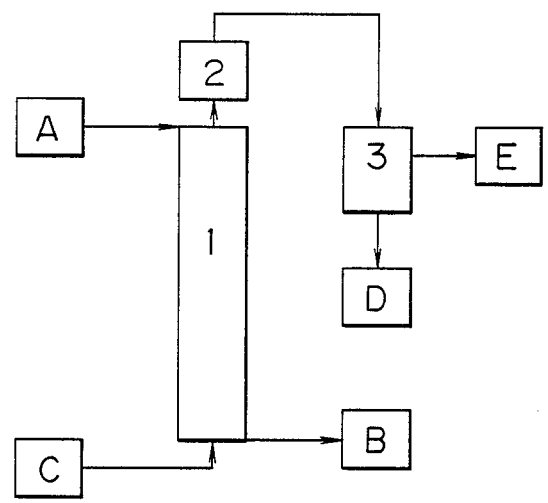
FIG. 1 shows an illustrative flow sheet of the method of Examples 2 to 19.

This invention provides a method for producing an aliphatic O-arylurethane from an aliphatic primary amine comprising (a) reacting an aliphatic primary amine with an aromatic hydroxyl compound and urea, and (b) carrying out the reaction while removing the ammonia by-produced from the reaction system so that the ammonia concentration of the reaction solution is maintained at 2 wt% or less.

The aromatic hydroxyl compound used in practicing the present invention may be any of those in which a hydroxyl group is directly bonded to the aromatic group. For example, there may be mentioned phenol; various alkylphenols such as cresol (including isomers), xylenol (including isomers), ethylphenol (including isomers), propylphenol (including isomers), etc.; various alkoxyphenols such as methoxyphenol (including isomers), ethoxyphenol (including isomers), etc; halogenated phenols such as chlorophenol (including isomers), bromophenol (including isomers), dichlorophenol (including isomers), dibromophenol (including isomers), etc.; alkyl and halogen-substituted phenols such as methylchlorophenol (including isomers), ethylchlorophenol (including isomers), methylbromophenol (including isomers), ethylbromophenol (including isomers), etc.; various substituted phenols represented by the formula

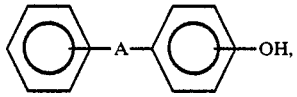

wherein A represents a single bond or a divalent group such as —O—, —S—, —SO$_2$—, —CO—, —CH$_2$—, or —C(R$_2$)—, in which R$_2$ is a lower alkyl group of one to six carbon atoms, and at least one hydrogen atom of the aromatic ring can be substituted with a substituent such as a halogen atom, a lower alkyl group of one to six carbon atoms, a lower alkoxy group of one to six carbon atoms, a lower alkyl ester group of two to six carbon atoms, an amide group and a cyano group; naphthol (including isomers) and various substituted naphthols; heteroaromatic hydroxyl compounds such as hydroxypyridine (including isomers), hydroxycoumarin (including isomers), hydroxyquinoline (including isomers), etc.; aromatic dihydroxyl compounds such as hydroquinone, resorcinol, catechol and their alkylsubstituted derivatives, etc.; aromatic dihydroxyl compounds represented by the formula

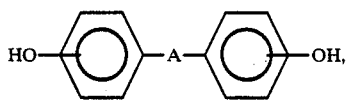

wherein A represents a single bond or a divalent group such as —O—, —S—, —SO$_2$—, —CO—, —CH$_2$—, or —C(R$_2$)—, in which R$_2$ is a lower alkyl group, and at least one hydrogen atom of the aromatic ring can be substituted with a substituent such as a halogen atom, a lower alkyl group of one to six carbon atoms, a lower alkoxy group of one to six carbon atoms, a lower alkyl ester group of two to six carbon atoms, an amide group and a cyano group; nitro-substituted aromatic hydroxyl compounds such as nitrophenol (including isomers), nitronaphthol (including isomers), etc.; and cyano-substituted aromatic hydroxyl compounds such as cyanophenol (including isomers), cyanonaphthol (including isomers), etc.

These aromatic hydroxyl compounds may be used individually or in combination. Of these compounds, aromatic monohydroxyl compounds are preferred because they can be distilled off easily and separated from the reaction mixture. Particularly, preferred are phenols having low boiling points.

The amount of the aromatic hydroxyl compound used in practicing the present invention is preferably one mol or more in terms of the hydroxyl group per mol of the amino group of the aliphatic primary amine used. When the amount of the aromatic hydroxyl compound is less than one mol in terms of the hydroxyl group per mol of the amino group of the aliphatic primary amine, undesirable substituted urea compounds are produced as by-products. A more preferred amount is 5 mols or more in terms of the hydroxyl group per mol of the amino group, and a most preferred amount is 10 mols or more as the hydroxyl group. Particularly, when an aliphatic primary polyamine and an aromatic polyhydroxyl compound are used, urea compounds having complicated substituents are produced as by-products as the amount of the hydroxyl group approaches one mol per mol of the amino group, so that it is preferred that the amount of the hydroxyl group is more than 5 mols per mol of the amino group. Preferred combinations, in this sense, of the aliphatic primary amine with the aromatic hydroxyl compound are the combination of an aliphatic primary monoamine with an aromatic monohydroxyl compound or/and aromatic polyhydroxyl compound and that of an aromatic monohydroxyl compound with an aliphatic primary monoamine or/and aliphatic primary polyamine. Also, the amount of the aromatic hydroxyl compound is preferably 100 mols or less per the amino group of the aliphatic primary amine. When the amount is more than 100 mols, it is not practical to practice the method industrially because the space time yield of the desired urethane becomes lower.

The aliphatic primary amine used in the present invention may be any of those in which one or more primary amino groups are bonded to aliphatic carbon atoms, and may be an alicyclic or an aralkyl primary amine.

Such aliphatic primary monoamines and polyamines include, for example, aliphatic primary monoamines such as methylamine, ethylamine, propylamine (including isomers), butylamine (including isomers), pentylamine (including isomers), hexylamine (including isomers), dodecylamine (including isomers), etc.; aliphatic primary diamines such as ethylenediamine, diaminopropane (including isomers), diaminobutane (including isomers), diaminopentane (including isomers), diaminohexane (including isomers), diaminodecane (including isomers), etc.; aliphatic primary triamines such as 1,2,3-triaminopropane, triaminohexane (including isomers), triaminononane (including isomers), triaminododecane (including isomers), 1,8-diamino-4-aminomethyloctane, 2-aminoethyl-2,6-diaminocaproate, 1,3,6-triaminohexane, 1,6,11-triaminoundecane, etc.; alicyclic primary monoamines and polyamines such as cyclopropylamine, cyclobutylamine, cyclopentylamine, cyclohexylamine, diaminocyclobutane, diaminocyclohexane (including isomers), 3-aminomethyl-3,5,5-trimethylcyclohexylamine, triaminocyclohexane (including isomers), etc.; and aralkyl primary monoamines and polyamines such as benzylamine, di(aminomethyl)benzene (including isomers), aminomethylpyridine (including isomers), di(aminomethyl)pyridine (including isomers), aminomethylnaphthalene (including isomers), di(aminomethyl)naphthalene (including isomers), etc.

In the aliphatic, alicyclic and aromatic groups constituting the skeleton of these primary amines, at least one hydrogen atom may be substituted with a substituent such as a halogen atom, an alkyl group of one to six carbon atoms, an alkoxy group of one to six carbon atoms, an aryl group, a lower alkyl ester group of two to six carbon atoms, a sulfone group and cyano group. Also, the skeleton may contain an unsaturated bond, an ether bond, an ester bond, a thioether bond, a sulfone bond, ketone bond, etc.

The amount of urea used in the present invention is preferably 0.5 mol or more per mol of the amino group of the aliphatic primary amine. More preferably, the amount is from 0.8 to 2 mols (both inclusive) per mol of the amino group. When the amount of urea is less than 0.5 mol per mol of the amino group of the aliphatic primary amine, complicated urea compounds are produced as by-products. When the amount is more than 2 mols, unreacted urea is left behind.

In practicing the present invention, it is preferred to use an excess of the aromatic hydroxyl compound as the reaction medium. If necessary, other suitable solvents can be used. Exemplary solvents which can be employed include aliphatic hydrocarbons such as pentane, hexane, heptane, octane, decane, etc.; aromatic hydrocarbons such as benzene, toluene, xylene, mesitylene, etc.; nitriles such as acetonitrile, benzonitrile, etc.; sulfones such as sulfolane, methylsulfolane, dimethyl sulfone, etc.; ethers such as tetrahydrofuran, 1,4-dioxane, 1,2-dimethoxyethane, etc.; ketones such as acetone, methyl ethyl ketone, etc.; and esters such as ethyl acetate, ethyl benzoate, etc.

Further, the following solvents can also be employed: halogenated aromatic hydrocarbons such as chlorobenzene, dichlorobenzene, trichlorobenzene, fluorobenzene, chlorotoluene, chloronaphthalene, bromonaphthalene, etc.; halogenated aliphatic hydrocarbons such as chlorohexane, chlorocyclohexane, trichlorotrifluoroethane, methylene chloride, carbon tetrachloride, etc.; and halogenated alicyclic hydrocarbons.

In practicing the present invention, it is preferred by carry out the reaction in a temperature range of from 150° to 280° C. When the reaction is carried out at a temperature below 150° C., the aliphatic primary amine, ammonia and urea bind strongly with the aromatic hydroxyl compound. As a result, the reaction is delayed or hardly proceeds, or the amount of the complicated substituted urea compounds increases. When the reaction is carried out at a temperature higher than 280° C., urea decomposes, the aromatic hydroxyl compound is modified in nature by dehydrogenation, or the yield of the desired aliphatic O-arylurethane lowers because of thermal decomposition, or thermal denaturalization. In this sense, a more preferred temperature range is from 180° C. to 260° C., and the most preferred range is from 200° C. to 250° C.

In practicing the present invention, the amount of ammonia to be removed, a by-product produced in the reaction system, varies to some degree with the reaction temperature and the difference in basicity between the aliphatic primary amine and aromatic hydroxyl compound, but it is almost constant independently of the composition of the reaction system. It is very important to remove the ammonia so that the ammonia concentration of the reaction solution is 2 wt% or less, because when the ammonia concentration is more than 2 wt%, the aliphatic O-arylurethanes are hardly obtained owing to the equilibrium shown in equation (I). Further, in order to increase the yield of the aliphatic O-arylurethanes, it is preferred to remove the ammonia so that the ammonia concentration of the reaction solution is 1 wt% or less. More preferably, the ammonia concentration of the reaction solution is 0.5 wt% or less.

One of the preferred embodiments for removing ammonia produced as a by-product from the reaction system is a reaction distillation method. In this method, the ammonia produced with the progress of the reaction can be removed immediately in a gaseous form from the reaction system by distillation. In order to accelerate the distillation rate of the ammonia, this method may be carried out with boiling of the solvent or aromatic hydroxyl compound.

Another preferred embodiment for removing the ammonia produced as a by-product from the reaction system is a method using an inert gas. In this method, the ammonia produced as the reaction proceeds can be removed from the reaction system by removing the ammonia accompanied by the inert gas. Such inert gas includes, for example, nitrogen, helium, argon, carbon dioxide gas, methane, ethane, propane, etc. It is also preferred to introduce these gases individually or in combination into the reaction system.

An organic solvent having a lower boiling point and being gaseous at a relatively lower temperature can also be used for removal of the by-produced ammonia from the reaction system in a similar way to with the use of an inert gas. As examples of such organic solvent, mention will be made of halogenated hydrocarbons (e.g. dichloromethane, chloroform, carbon tetrachloride), lower hydrocarbons (e.g. pentane, hexane, heptane, benzene, toluene, xylene), ketones (e.g. acetone, methyl ethyl ketone), ethers (e.g. tetrahydrofuran, dioxane), etc.

Further, it is also possible to use a catalyst for the purpose of lowering the temperature or accelerating the reaction rate in the reaction distillation method or in the method using the inert gas. As the catalyst, for example the following are preferably used: rare earth elements, antimony, bismuth and the oxides, sulfides and salts of these elements; boron and boron compounds; metals belonging to the copper, zinc, aluminum, carbon and titanium groups of the periodic table and the oxides and sulfides of these metals; and the carbides and nitrides of the elements belonging to the carbon group (except carbon), titanium group, vanadium group and chromium group of the periodic table. When a catalyst is used, the amount of the catalyst and that of the aliphatic primary amine may be in any ratio, but it is preferred to use the catalyst in an amount of, generally, from 0.001 to 100 times by weight based on the weight of the aliphatic primary amine.

As another preferred embodiment for removing the ammonia by-produced from the reaction system, there is a method of separating ammonia by adsorption of the ammonia onto adsorbents. As such adsorbents, those which can be used at a temperature of from 150° to 280° C., for example silica, alumina and various kinds of zeolite and diatomaceous earth can be used.

In order to remove the ammonia by-produced from the reaction system, the foregoing reaction distillation method, method using inert gases, etc. and method using adsorbents can also be used in combination.

In practicing the present invention, the reaction pressure varies with the composition of the reaction system, reaction temperature, method for removing ammonia, kind of reaction apparatus, etc. Usually, however, it is preferred to carry out the reaction in a pressure range of from 0.1 to 50 atm., and a pressure range of from 1 to 30 atm. is preferred in terms of industrial practice. Similarly, the reaction time also varies with the composition of the reaction system, reaction temperature, method for removing ammonia, kind of reaction apparatus, etc. Usually, however, it is from one minute to 100 hours, more preferably from ten minutes to ten hours, with as short a reaction time as possible being preferred.

The type of reactor used in practicing the present invention is not limited at all. For example, the following types of reactors are preferably used: a vertical tubular reactor for advancing the reaction while passing the solution containing the raw materials downwardly through the tubular reactor, and for withdrawing and removing the ammonia by-produced from the top of the reactor; a vessel reactor for advancing the reaction and at the same time withdrawing and removing the ammonia by-produced in a gaseous form; and a combination of these types of reactors. Further, it is also preferred to install a distillation tower and/or partial condenser at the top of these reactors if necessary.

The reaction of the present invention can be carried out either batch-wise or continuously.

The method of the present invention is suitable to produce aliphatic O-arylmonourethanes and polyurethanes, and is also suitable to produce the following compounds used in large amounts in industry: 1,6-hexamethylene-O,O'-diphenylurethane which is the masked isocyanate of 1,6-hexamethylene diisocyanate, 3-phenoxycarbonylaminomethyl-3,5,5-trimethyl-1-phenoxycarbonylaminocyclohexane which is the masked isocyanate of 3-isocyanatemethyl-3,5,5-trimethylcyclohexylisocyanate (IPI), and m-xylylene-O,O'-diphenylurethane which is the masked isocyanate of m-xylylenediisocyanate.

As compared with conventional methods, the present invention has several advantages as follows:

(1) the aliphatic O-arylurethanes can be obtained in high yields by carrying out the reaction while the ammonia by-produced is forcibly removed from the reaction system so that the ammonia concentration of the reaction solution is maintained at 2 wt% or less;

(2) because phosgene and carbon monoxide are not used, there are no troublesome problems of corrosion and toxicity or of a hydrogen chloride gas, as a by-product, being produced in large amounts. Further, the cost is low because there is no necessity to use expensive noble metal catalysts; and (3) the process is simple because the reaction is carried out in one step, and because the urethane yield is high, it is advantageous to carry out the process industrially. Further, because the resulting urethanes are aliphatic O-arylurethanes, their thermal dissociation is easy, and therefore, they can advantageously be used as masked isocyanates or as precursors of aliphatic isocyanates.

The present invention will be illustrated in more detail with reference to the following examples, but it is not limited to these examples.

Determination of ammonia in the reaction solution:

The reaction solution was extracted with water of 10 times by weight or more based on the reaction solution to obtain an aqueous solution, and ammonium ions in the resulting solution were quantitatively determined by ion chromatography (IC). The column and detector used for ion chromatography were TSK-gel IC-Cation and CM-8000, respectively (produced by Toso Co. Ltd.), and measurement was carried out at 35° C. while a 2 mM aqueous conc. nitric acid solution, an eluent, was being passed through the column at a rate of 1.2 ml/min.

Determination of ammonia in the reaction gas was carried out by gas chromatography (GC).

Determinations of the aromatic hydroxyl compound and aliphatic primary amine were carried out by gas chromatography (GC) and liquid chromatography (LC).

Determinations of urea and the aliphatic O-arylurethane were carried out by gel permeation chromatography (GPC) and liquid chromatography (LC).

EXAMPLE 1

To a 1000-ml, four-necked glass flask equipped with a thermometer, stirrer, reflux condenser and gas inlet tube were added 29 g of 1,6-hexamethylenediamine (hereinafter frequently abbreviated as HDA), 33 g of urea and 470 g of phenol, and reaction was carried out with stirring, during which 20 liters/hour (at normal temperature and pressure, hereinafter frequently abbreviated as N.T.P.) of nitrogen gas was bubbled into the flask through a ball filter reaching to the bottom of the flask and the phenol was boiled at from 170° C. to 180° C. Thereafter, the following operation was repeated every 20 hours: first, the whole reaction solution was recovered and weighed (g), and then 1.0 g of the solution was sampled and quantitatively determined for the weight percentages of 1,6-hexamethylene O,O'-diphenylurethane (hereinafter frequently abbreviated as HDPh) and ammonia (NH$_3$) contained in it. The yield (%) of 1,6-hexamethylene-O,O'-diphenylurethane was calculated based on the HDA used.

TABLE 1

| Reaction time (hr) | Composition of the reaction solution | | Amount recovered (g) | Yield of HDPh (%) |
|---|---|---|---|---|
| | HDPh (%) | NH$_3$ (%) | | |
| 20 | 10.3 | 0.2 | 486 | 56 |
| 40 | 15.5 | 0.1 | 447 | 78 |
| 60 | 18.8 | 0.04 | 407 | 86 |
| 80 | 21.2 | 0.01 | 378 | 90 |

140 Grams of the distillate containing phenol and ammonia was obtained from the top of the reflux condenser after 80 hours. From this result, it is apparent that the reaction distillation of phenol and ammonia occurred in combination with the release of the ammonia accompanied with the inert gas.

The results are shown in Table 1. Table 1 shows that 1,6-hexamethylene-O,O'-diphenylurethane is obtained in a high yield of 90% if the ammonia by-produced is compulsorily removed from the reaction solution until its concentration reaches 0.01 wt%, and also that the yield of 1,6-hexamethylene-O,O'-diphenylurethane decreases as the weight percent of the ammonia by-produced being present in the reaction solution increases. It is apparent, therefore, that an equilibrium exists in the reaction expressed by equation (I) and it lies far to the left (side of the starting materials).

COMPARATIVE EXAMPLE 1

The procedure of Example 1 was repeated except that nitrogen gas was not introduced. The reaction was continued for 80 hours at the refluxing temperature (179°–182° C.) under stirring. The reaction solution was found to contain 2.2 wt% of ammonia, but 1,6-hexamethylene-O,O'-diphenylurethane was not detected. Also, there were no effluents from the top of the reflux condenser.

After the reaction for 80 hours, 43 g of a yellowish brown solid matter was obtained by distilling off the phenol from the reaction mixture. This solid matter was extracted with dimethylacetamide, which is a good solvent for 1,6-hexamethylene-O,O'-diphenylurethane, but 1,6-hexamethylene-O,O'-diphenylurethane was not also detected at all in this extract.

COMPARATIVE EXAMPLE 2

The procedure of Comparative Example 1 was repeated except that 650 g of n-octanol, an alcohol, was used instead of the phenol. The reaction was continued for 20 hours at refluxing temperature (180°–182° C.) under stirring. After distillation of the n-octanol from the reaction mixture, 100 g of a pale yellow product was obtained. This product was found to contain 87 g of hexamethylene-di(n-octylurethane). The yield of 1,6-hexamethylene-O,O'-di(n-octylurethane) was 81% based on HDA used.

The results of Example 1 and Comparative Example 1 show that it is very difficult to remove the by-product ammonia from the reaction mixture in the reaction of an aliphatic primary amine with urea and an aromatic hydroxyl compound, and also that the desired aliphatic O-arylurethanes cannot be obtained unless the ammonia is removed effectively from the reaction system. In the case of Example 1, it was found that the reaction distillation method in combination with the use of an inert gas is very effective to remove the ammonia.

Further, Comparative Example 2 shows that aliphatic O-alkylurethanes can be obtained easily by the reaction of an aliphatic primary amine with an alcohol and urea because the ammonia produced as a by-product can be removed easily from the reaction system without using any special methods. However, in the case of Comparative Example 1, the reaction using an aromatic hydroxyl compound instead of an alcohol can never give aliphatic O-arylurethane, nevertheless the reaction was carried out under similar conditions. This means that the method for producing aliphatic O-arylurethanes is never predictable from the reaction for producing aliphatic O-alkylurethanes.

EXAMPLES 2 TO 10

These Examples show the continuous reaction distillation method in combination with the use of an inert gas.

Into a 2-liter vertical tubular reactor 1 packed with packings shown in FIG. 1, a solution of the raw materials A was continuously fed from the top of the reactor 1, and a reaction solution B was continuously recovered from the bottom of the reactor 1. Nitrogen gas C was introduced into the reactor 1 from the bottom, and gaseous components E were recovered through a reflux condenser 2 and a gas-liquid separator 3 from the top of the reactor 1; and at that time, a condensate D accompanying the gas was continuously recovered from the bottom of the gas-liquid separator 3.

The reaction was carried out under the following conditions. The solution A containing 464 g of HDA, 504 g of urea and 7,520 g of phenol was fed at the rate shown in Table 2.

The reaction temperature is also shown in Table 2.

The average contact time was between 5 and 30 minutes.

The reaction pressure was 6 atm. (12 atm. for Examples 9 and 10).

The temperature of the reflux condenser 2 was maintained at about 140° C.

The flow rate of nitrogen gas introduced was 20 liters/hour (at N.T.P.).

After completion of the reaction, the whole reaction solution B was recovered and weighted (g), and the weight percentages of 1,6-hexamethylene-O,O'-diphenylurethane (HDPh) and ammonia ($NH_3$) contained in the reaction solution B were determined. From these values, the yield (%) of 1,6-hexamethylene-O,O'-diphenylurethane based on HDA fed was calculated. The results are shown in Table 2.

TABLE 2

| Example | Temperature (°C.) | Feed rate of A (g/hr) | Composition of the reaction solution B | | Total weight (g) | Yield of HDPh (%) |
|---|---|---|---|---|---|---|
| | | | HDPh (%) | $NH_3$ (%) | | |
| 2 | 220 | 100 | 17.0 | 0.01 | 7708 | 92 |
| 3 | 220 | 200 | 12.7 | 0.1 | 7956 | 71 |
| 4 | 220 | 400 | 6.5 | 0.4 | 8144 | 37 |
| 5 | 220 | 800 | 3.4 | 1.0 | 8235 | 20 |
| 6 | 210 | 800 | 1.7 | 2.0 | 8323 | 10 |
| 7 | 150 | 100 | 1.7 | 0.03 | 8424 | 10 |
| 8 | 180 | 100 | 4.2 | 1.1 | 8198 | 24 |
| 9 | 260 | 100 | 14.7 | 0.01 | 7740 | 82 |
| 10 | 280 | 100 | 3.1 | 0.03 | 7350 | 16 |

The results of Example 2 show that 1,6-hexamethylene-O,O'-diphenylurethane can be obtained continuously in a high yield of 92% by removing the ammonia by-produced compulsorily from the reaction solution until the ammonia concentration is reduced to 0.01 wt%.

Also, the results of Examples 2 to 6 show the following.

(1) The yield of 1,6-hexamethylene-O,O'-diphenylurethane increases as ammonia, a by-product, is removed from the reaction solution.

(2) In order to obtain 1,6-hexamethylene-O,O'-diphenylurethane, the by product ammonia, should be removed from the reaction solution until the ammonia concentration is reduced to 2 wt%.

(3) In order to obtain 1,6-hexamethylene-O,O'-diphenylurethane in a yield of 20% or more, it is preferred to remove the by product ammonia from the reaction solution until the ammonia concentration is reduced to 1 wt% or less.

(4) In order to obtain 1,6-hexamethylene-O,O'-diphenylurethane in higher yields, it is preferred to remove the by product ammonia from the reaction solution until the ammonia concentration is reduced to 0.5 wt% or less.

Further, from a comparison of Example 2 with Examples 7 to 10, it was found that, in order to obtain 1,6-hexamethylene-O,O'-diphenylurethane, the reaction temperature is preferably in a range of from 150° to 280° C., and also that, in order to obtain high yields, the reaction temperature is more preferably in a range of from 180° to 260° C.

EXAMPLE 11

This example was carried out following the procedure of Example 2 under the following reaction conditions.

The solution A containing 464 g of HDA, 504 g of urea and 8,640 g of m-cresol was fed at a rate of 100 g/hour.

The reaction temperature and pressure were 220° C. and 6 atm, respectively.

The flow rate of nitrogen gas introduced was 20 liters/hour (at N.T.P.).

After completion of the reaction, 8,880 g of the reaction solution B was recovered. This solution was found to contain 15.9 wt% of 1,6-hexamethylene-O,O'-di(m-cresylurethane) and 0.01 wt% of ammonia. The yield of 1,6-hexamethylene-O,O'-di(m-cresylurethane) based on HDA fed was 93%.

EXAMPLE 12

The procedure of Example 11 was repeated except using a solution A comprising 464 g of HDA, 504 g of urea and 10,280 g of o-chlorophenol.

After completion of the reaction, 9,625 g of the reaction solution B was recovered. This solution was found to contain 13.5 wt% of 1,6-hexamethylene-O,O'-di(o-chlorophenylurethane) and 0.01 wt% of ammonia. The yield of 1,6-hexamethylene-O,O'-di(o-chlorophenylurethane) based on HDA fed was 91%.

EXAMPLE 13

The procedure of Example 11 was repeated except using a solution A comprising 464 g of HDA, 504 g of urea and 11,520 g of 2-naphthol.

After completion of the reaction, 11,457 g of the reaction solution B was recovered. This solution was found to contain 14.0 wt% of 1,6-hexamethylene-O,O'-di(2-naphthylurethane) and 0.01 wt% of ammonia. The yield of 1,6-hexamethylene-O,O'-di(2-naphthylurethane) based on HDA fed was 89%.

EXAMPLE 14

The procedure of Example 11 was repeated except using a solution A comprising 680 g of 3-aminomethyl-3,5,5-trimethylcyclohexylamine (IPA), 504 g of urea and 7,520 g of phenol.

After completion of the reaction, 7,931 g of the reaction solution B was recovered. This solution was found to contain 18.2 wt% of 3-phenoxycarbonylaminomethyl-3,5,5-trimethyl-1-phenoxycarbonylaminocyclohexane and 0.01 wt% of ammonia. The yield of 3-phenoxycarbonylaminomethyl-3,5,5-trimethyl-1-phenoxycarbonylaminocyclohexane based on IPA fed was 89%.

EXAMPLE 15

The procedure of Example 11 was repeated except using a solution A comprising 544 g of m-xylylenediamine, 504 g of urea and 7,520 g of phenol.

After completion of the reaction, 7,690 g of the reaction solution B was recovered. This solution was found to contain 18.8 wt% of m-xylylene-O,O'-diphenylurethane and 0.01wt% of ammonia. The yield of m-xylylene-O,O'-diphenylurethane based on m-xylylenediamine fed was 96%.

EXAMPLE 16

The procedure of Example 11 was repeated except that a solution A comprising 516 g of n-octylamine, 257 g of urea and 3,760 g of phenol was used, and that nitrogen gas was introduced at a flow rate of 10 liters/hour (at N.T.P.).

After completion of the reaction, 4,097 g of the reaction solution B was recovered. This solution was found to contain 23.6 wt% of n-octyl-O-phenylurethane and 0.01 wt% of ammonia. The yield of n-octyl-O-phenylurethane based on n-octylamine fed was 97%.

EXAMPLE 17

The procedure of Example 16 was repeated except using a solution A comprising 516 g of n-octylamine, 257 g of urea and 3,720 g of 4,4'-dihydroxybiphenyl.

After completion of the reaction, 4,353 g of the reaction solution B was recovered. This solution was found to contain 21.8 wt% of 4,4'-di(n-octylcarbamoyloxy)biphenyl and 0.01 wt% of ammonia. The yield of 4,4'-di(n-octylcarbamoyloxy)biphenyl based on n-octylamine fed was 48%.

EXAMPLE 18

This example was carried out following the procedure of Example 2 using an 8-liter vertical tubular reactor 1 packed with packings under the following reaction conditions.

A solution A containing 464 g of HDA, 504 g of urea and 15,040 g of phenol was fed at a rate of 1,500 g/hour. The reactor temperature and pressure were 235° C. and 4.2 atm, respectively.

The average contact time was 30 minutes.

The temperature of the reflux condenser 2 was kept about 100° C.

The flow rate of nitrogen gas introduced was 100 liters/hour (at N.T.P.).

After completion of the reaction, 15,119 g of the reaction solution B was recovered. This solution was found to contain 9.23 wt% of 1,6-hexamethylene-O,O'-diphenylurethane and 0.004 wt% of ammonia. The yield of 1,6-hexamethylene-O,O-diphenylurethane based on HDA fed was 98%. Until completion of the reaction, 1,435 liters (at N.T.P.) of the gaseous components E was recovered. The ammonia gas content in the gaseous components E was found to be 25 vol. % by gas chromatography, which means that the ammonia could be recovered in the gaseous state in an amount of 99% of the theoretical amount.

Further, the phenol was removed from the reaction solution B by means of a rotary evaporator to obtain 1,560 g of a pale yellow solid. This solid was dissolved in 3 liters of xylene at 100° C. and recrystallized to obtain 1,350 g of a white solid. The purity of 1,6-hexamethylene-O,O'-diphenylurethane was 99 wt% by GPC analysis.

EXAMPLE 19

The procedure was carried out in the same manner as in Example 18 except that n-hexane was used in place of the nitrogen gas. 385 Grams/hour of n-hexane was introduced in a gaseous state into the bottom of the vertical tubular reactor 1 through an evaporator. After completion of the reaction, 15,213 g of the reaction solution B was recovered. This solution was found to contain 9.08 wt% of 1,6-hexamethylene-O,O'-diphenylurethane and 0.004 wt% of ammonia. The yield of 1,6-hexamethylene-O,O'-diphenylurethane based on HDA fed was 97%. Further, the phenol was removed from the reaction solution by means of a rotary evaporator, and the residue was recrystallized at 100° C. from 3 liters of xylene to obtain 1,336 g of a white solid. The purity of 1,6-hexamethylene-O,O'-diphenylurethane was 99 wt% by GPC analysis.

What is claimed is:

1. A method for producing an aliphatic O-arylurethane from an aliphatic primary amine which comprises
    (a) reacting an aliphatic primary amine with an aromatic hydroxyl compound and urea, and
    (b) carrying out the reaction while removing ammonia by-produced in the reaction from the reaction system so that the ammonia concentration of the reaction solution is maintained at 2 wt% or less.
2. A method according to claim 1, wherein the range of the reaction temperature is from 150° C. to 280° C.
3. A method according to claim 1, wherein the range of the reaction temperature is from 180° C. to 260° C.
4. A method according to any one of claims 1 to 3, wherein ammonia is removed so that the ammonia concentration of the reaction solution is maintained at 1 wt% or less.
5. A method according to any one of claims 1 to 3, wherein ammonia is removed so that the ammonia concentration of the reaction solution is maintained at 0.5 wt% or less.
6. A method according to any one of claims 1 to 3, wherein the aliphatic primary amine is an aliphatic, alicyclic or aralkyl primary monoamine or polyamine.
7. A method according to claim 6, wherein the aliphatic primary amine is a diamine.
8. A method according to any one of claims 1 to 3, wherein the aromatic hydroxyl compound is an aromatic monohydroxyl compound.
9. A method according to claim 8, wherein the aromatic hydroxyl compound is phenol.
10. A method according to any one of claims 1 to 3, wherein ammonia is removed by distillation.
11. A method according to any one of claims 1 to 3, wherein ammonia is removed using an inert gas or a low-boiling organic solvent.
12. A method according to any one of claims 1 to 3, wherein the aromatic hydroxyl compound is phenol, the aliphatic primary amine is 1,6-hexamethylenediamine, and the aliphatic O-arylurethane to be produced is 1,6-hexamethylene-O,O'-diphenylurethane.
13. A method according to claim 10 wherein the aromatic hydroxyl compound is phenol, the aliphatic primary amine is 1,6-hexamethylenediamine, and the aliphatic O-arylurethane to be produced is 1,6-hexamethylene-O,O'-diphenyl-urethane.
14. A method according to claim 11 wherein the aromatic hydroxyl compound is phenol, the aliphatic primary amine is 1,6-hexamethylenediamine, and the aliphatic O-arylurethane to be produced is 1,6-hexamethylene-O,O'-diphenyl-urethane.

* * * * *